United States Patent [19]

Kukolja et al.

[11] 4,031,084

[45] June 21, 1977

[54] PROCESS FOR CEPHALOSPORIN ANTIBIOTIC INTERMEDIATES

[75] Inventors: Stjepan Kukolja; Douglas O. Spry, both of Indianapolis, Ind.

[73] Assignee: Eli Lilly and Company, Indianapolis, Ind.

[22] Filed: Oct. 23, 1975

[21] Appl. No.: 625,281

[52] U.S. Cl. .......................................... 260/243 C
[51] Int. Cl.² .................................... C07D 501/04
[58] Field of Search ............................... 260/243 C

[56] References Cited

UNITED STATES PATENTS

| | | | |
|---|---|---|---|
| 3,668,201 | 6/1972 | Gutowski | 260/243 C |
| 3,668,202 | 6/1972 | Foster et al. | 260/243 C |
| 3,917,587 | 11/1975 | Chauvette | 260/243 C |

*Primary Examiner*—Nicholas S. Rizzo
*Attorney, Agent, or Firm*—William B. Scanlon; Everet F. Smith

[57] ABSTRACT

7-Acylamido-3-exomethylenecepham ester sulfoxides are reacted with ozone to provide the corresponding 3-hydroxy-3-cephem ester sulfoxides, intermediates for 3-methoxy and 3-halo substituted cephalosporin antibiotics; e.g., p-nitrobenzyl 7-phenoxyacetamido-3-exomethylenecepham-4-carboxylate-1-oxide provides the corresponding 3-hydroxy-3-cephem ester sulfoxide.

10 Claims, No Drawings

PROCESS FOR CEPHALOSPORIN ANTIBIOTIC INTERMEDIATES

BACKGROUND OF THE INVENTION

New cephalosporin antibiotics substituted directly on the $C_3$ carbon atom of the cephem nucleus with methoxy and halo groups are described by R. R. Chauvette and P. A. Pennington, *J. Am. Chem. Soc.*, 96, 4986 (1974). As described therein, the 3-halo and 3-methoxy-substituted-cephalosporins are prepared from 3-exomethylenecepham esters by ozonolysis of the 3-exomethylene double bond. The product of the ozonlysis, a 3-"oxo" 3-cephem ester, is characterized as a 3-hydroxy-3-cephem ester which can also exist in its tautomeric keto form. The 3-methoxy substituted cephalosporin is prepared by reacting the 3-hydroxy-3-cephem ester with diazomethane while the 3-halo cephalosporin is prepared by halogenating the 3-hydroxy ester intermediate.

The 3-exomethylenecepham cephalosporin esters employed as starting materials in the synthesis of the 3-halo and 3-methoxy substituted cephalosporins are described in *J. Org. Chem.*, 38, 2994 (1973).

Accordingly, the 3-hydroxy-3-cephem esters are valuable intermediates useful in the preparation of the 3-methoxy and 3-halo cephalosporin antibiotic compounds.

In the co-pending application of R. R. Chauvette Ser. No. 310,191 filed Nov. 28, 1972, now U.S. Pat. No. 3,917,587 the ozonolysis of 3-exomethylenecepham esters to 3-hydroxy-3-cephem esters is described. The 3-exomethylenecepham esters, employed as starting materials in the process have the sulfur of the dihydrothiazine ring in the sulfide or unoxidized divalent state. The 3-hydroxy-3-cephem ester products obtained in the disclosed process also have the sulfur atom of the dihydrothiazine ring in the divalent unoxidized state, and suffer from certain disadvantages. For example, they tend to undergo over-oxidation during the ozonolysis to form the corresponding sulfoxide. The presence of the sulfoxide complicates the isolation and purification of the 3-hydroxy-3-cephem ester product. Further, the 3-hydroxy-3-cephem esters exhibit instability. Consequently, when used as intermediates to the 3-methoxy or 3-halo antibiotics, the 3-hydroxy-3-cephem esters are best employed soon after their preparation and isolation in the described process.

SUMMARY

This invention relates to a process for preparing cephalosporin compounds. In particular, it relates to a process for the preparation of 3-hydroxy-3-cephem ester sulfoxides, useful intermediates for the preparation of cephalosporin antibiotics.

According to the process of this invention, an ester of a 7-acylamido-3-exomethylenecepham sulfoxide is reacted at a temperature between about $-90°$ and $20°$ C. in an inert aprotic solvent with at least two molar equivalents of ozone, optionally in the presence of a co-solvent proton source, to provide a 7-acylamido-3-hydroxy-3-cephem-4-carboxylic acid ester sulfoxide. The ozonolysis product, the 3-hydroxy cephem ester sulfoxide, is isolated directly from the reaction mixture in high yields and in a high state of purity. The intermediate oxidation products formed in situ during ozonolysis can be decomposed either thermally or by addition of a mild reducing agent to the reaction mixture prior to isolation of the 3-hydroxy product.

DETAILED DESCRIPTION

In the process of this invention, a 3-exomethylenecepham ester sulfoxide represented by the following general formula

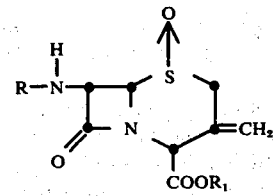

is reacted in an inert solvent at a temperature between about $-90°$ and $20°$ C. with at least two molar equivalents of ozone to provide a 3-hydroxy-3-cephem ester sulfoxide represented by the following structural formula

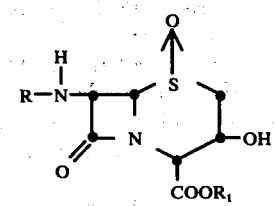

In the above formulas, R can be any group which serves to protect the 7-amino group and which preferably is itself unreactive with ozone. $R_1$ is an ester group serving to block the $C_4$ carboxylic acid group.

The amino-protecting group R can be any of the commonly employed amino-protecting groups of the penicillin and cephalosporin art, for example R can be p-nitrobenzyloxycarbonyl, t-butyloxycarbonyl, 2,2,2-trichloroethoxycarbonyl, the triphenylmethyl group, or R can be represented by $H_2^+$, wherein the 7-amino group is protected by salt formation, for example salts formed with the mineral acids such as hydrochloric acid and hydrobromic acid or with organic acids such as methanesulfonic, benzenesulfonic, and p-toluenesulfonic acid.

Preferred cephalosporin starting materials in the process of this invention are those wherein R represents an ozone inert acyl moiety derived from a carboxylic acid. An ozone-inert acyl function represented by R is one which is non-reactive with ozone, for example one which does not contain an oxidizable function such as a carbon to carbon double bond of an alkene or an oxidizable sulfur atom or or other oxidizable functional group. Such groups containing ozone-reactive functions interfere with the ozonization of the primary oxidation site in the molecule and can provide side products which interfere with the isolation of the desired product.

Examples of these acyl groups are alkanoyl such as acetyl and formyl; substituted alkanoyl such as chloroacetyl and cyanoacetyl; aroyl such as benzoyl and substituted benzoyl, for example, 2,6-dimethoxybenzoyl; phenylalkanoyl and substituted phenylalkanoyl, for example, phenylacetyl, 4-chlorophenylacetyl, lower alkyl substituted phenylacetyl, 4-methoxyphenylacetyl, and 3- or 4-hydroxyphenylacetyl; $\alpha$-substituted phenylacetyl wherein the $\alpha$-substituent is amino, hydroxy, formyloxy, acetoxy, —SO₃H, —SO₂NH₂, carboxyl and ester derivatives thereof; aryloxy-substituted-alkanoyl such as phenoxyacetyl, 2-phenoxypropionyl, naphthyloxyacetyl and the lower alkyl, lower alkoxy, halo, nitro, and hydroxy derivatives thereof; and heterocyclic substituted alkanoyl such as 2-furylacetyl, 2-oxazoleacetyl, tetrazoleacetyl, 2-sydnoneacetyl, pyrrole-2-acetyl; and like acyl groups. The 7-amino group of the starting material can also be protected during the process with diacyl groups such as phthaloyl and succinoyl.

The aforementioned acyl groups can be the 7-position side chain desired in the final 3-halo or 3-methoxy antibiotic or, alternatively, it can be one selected as a desirable side chain for use in the process. In the latter instance the side-chain can be removed after the ozonolysis and methoxylation or halogenation to provide the 7-amino-3-methoxy or 3-halo-3-cephem-4-carboxylic acid ester sulfoxide. The side-chain in the 7-position is removed according to the well known N-deacylation method for example as described by U.S. Pat. No. 3,549,628. This method employs a phosphorus halide such as PCl₅ in an inert solvent to form in situ the imino chloride of the amide linkage of the side chain. The imino chloride is coverted to an unstable imino ether with an alcohol such as methanol, and decomposition or hydrolysis of the imino ether affords the 7-amino ester.

The 7-amino-3-hydroxy-3-cephem ester sulfoxide thus obtained can then be reacylated with the desired carboxylic acid by following conventional acylation procedures.

Following the acylation, the carboxylic acid protecting group is removed to provide the desired N-acyl-3-methoxy or 3-halo substituted antibiotic in the free acid form.

Preferred 3-exomethylenecepham ester sulfoxide starting materials in the process of this invention are represented by the following formula

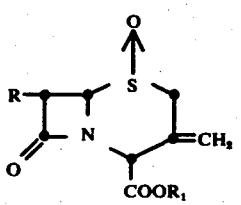

wherein R is H₃N⁺—, phthalimido, succinimido, an acylamido group of the formula

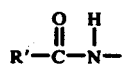

wherein R' is hydrogen, C₁ – C₆ alkyl, cyanomethyl, halomethyl; or an acylamido group of the formula

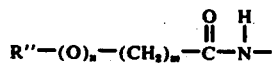

wherein R'' is phenyl or phenyl substituted by halogen, C₁–C₄ lower alkyl, C₁–C₄ lower alkoxy, nitro or carboxy, and m and n are independently 0 or 1; or R is a substituted arylacylamido group of the formula

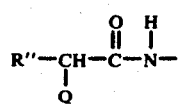

wherein R'' has the same meanings as defined above and Q is protected hydroxy, protected amino, carboxy, —SO₂NH₂, or the group —SO₃H; and R₁ is a carboxylic acid protecting group.

In the above description of the preferred compounds of this invention, the term C₁–C₆ alkyl "alkyl" refers to the straight and branched chain saturated alkyl groups such as methyl, ethyl, propyl, isopropyl, n-butyl, isobutyl, n-pentyl, n-hexyl and the like; haloalkyl refers to chloromethyl and bromomethyl. When in the above definition R'' represents a substituted phenyl group, R'' can be a mono or disubstituted halophenyl group such as 4-chlorophenyl, 3-chlorophenyl, 3,4-dichlorophenyl, 4-bromophenyl, 2-fluorophenyl, and like halophenyl groups; a mono or dialkylphenyl group such as the 2-, 3-, and 4-methylphenyl groups, 4-ethylphenyl, 4-isopropylphenyl, and like groups; the alkoxyphenyl groups for example 2-methoxyphenyl, 3,4-dimethoxyphenyl, 4-isopropoxyphenyl, 3-methoxy-4-ethoxyphenyl, and the like; nitrophenyl such as 2-, 3-, and 4-nitrophenyl groups; and R'' represents the carboxy substituted phenyl groups such as 4-carboxyphenyl, 3-carboxyphenyl, 3-methyl-4-carboxyphenyl, 3-chloro-4-carboxyphenyl, and like substituted phenyl groups.

The term "protected amino" as used herein has reference to an amino group substituted with one of the commonly employed amino-protecting groups such as the t-butyloxycarbonyl group, the benzyloxycarbonyl group, the p-methoxybenzyloxycarbonyl group, the p-nitrobenzyloxycarbonyl group, the 2,2,2-trichloroethoxycarbonyl group, and like amino-protecting groups. The term "protected hydroxy" refers to the readily cleavable groups employed in the art to protect an hydroxyl group, for example the formyl group, the chloroacetyl group, the benzhydryl group, the trityl group, and the p-nitrobenzyloxycarbonyl group.

The term R₁ represents ester forming groups which protect or block the carboxylic acid group during the ozonolysis. A large number of such groups are known in the art and include for example, tri-haloethyl such as 2,2,2-trichloroethyl and 2,2,2-tribromoethyl; arylmethyl and substituted arylmethyl, e.g., benzyl, diphenylmethyl, 4-methoxybenzyl, 4-nitrobenzyl, 3,5-dimethoxybenzyl, 3,5-dimethoxy-4-hydroxybenzyl; phenacyl; t-butyl and methoxymethyl. The esters formed with such groups are characterized by the ease with which they can be removed under acid or basic hydrolysis or hydrogenolysis conditions.

Illustrative of the acylamido groups represented by R in the above formula are the following: acetamido, butyramido, chloroacetamido, cyanoacetamido, benzamido, 2,6-dimethoxybenzamido, 4-chlorobenzamido, phenylacetamido, 4-nitrophenylacetamido, 4-methylphenylacetamido, 2,4-dichlorophenylacetamido, 4-bromophenylacetamido, 4-methoxyphenylacetamido, phenoxyacetamido, 4-methylphenoxyacetamido, 3-chlorophenoxyacetamido, the protected mandelamido groups represented by the formula

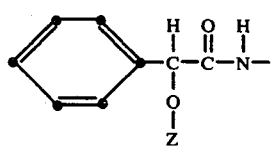

wherein Z is for example, formyl, acetyl, chloroacetyl, dichloroacetyl, benzyloxycarbonyl, 4-nitrobenzyloxycarbonyl, and wherein the phenyl group of the protected mandelamido group can be mono or di-substituted as defined for R''; the amino-protected phenylglycylamino groups represented by the formula

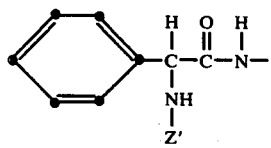

wherein Z' is an amino protecting group, for example, t-butyloxycarbonyl, 2,2,2-trichloroethoxycarbonyl, 4-nitrobenzyloxycarbonyl, and the like; the phenylmalonamido group

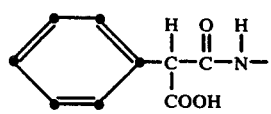

wherein the phenyl group can be substituted as defined for R''; and the α-sulfo substituted phenylacetamido group of the formula

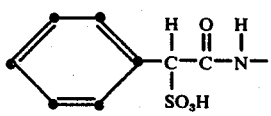

wherein the phenyl ring can be substituted as defined for R'' above.

Representative of the 3-exomethylenecepham ester sulfoxides which can be used in the process of this invention are the following: p-nitrobenzyl 7-phenylacetamido-3-exomethylenecepham-4-carboxylate-1-oxide, p-nitrobenzyl 7-phenoxyacetamido-3-exomethylenecepham-4-carboxylate-1-oxide, diphenylmethyl 7-acetamido-3-exomethylenecepham-4-carboxylate 1-oxide, p-methoxybenzyl 7-benzamido-3-exomethylenecepham-4-carboxylate-1-oxide, 2,2,2-trichloroethyl 7-phenoxyacetamido-3-exomethylenecepham-4-carboxylate-1-oxide, benzyl 7-benzamido-3-exomethylenecepham-4-carboxylate-1-oxide, diphenylmethyl 7-(2-formyloxy-2-phenylacetamido)-3-exomethylenecepham-4-carboxylate-1-oxide, 4-nitrobenzyl 7-(2-t-butyloxycarbamido-2-phenylacetamido)-3-exomethylenecepham-4-carboxylate-1-oxide, 2,2,2-trichloroethyl 7-(2-carboxy-2-phenylacetamido)-3-exomethylenecepham-4-carboxylate-1-oxide, 4-nitrobenzyl 7-(2-sulfo-2-phenylacetamido)-3-exomethylenecepham-4-carboxylate-1-oxide, p-nitrobenzyl 7-phthalimido-3-exomethylenecepham-4-carboxylate-1-oxide, benzyl 7-succinimido-3-exomethylenecepham-4-carboxylate-1-oxide, methoxymethyl 7-propionamido-3-exomethylenecepham-4-carboxylate-1-oxide, p-methoxybenzyl 7-chloroacetamido-3-exomethylenecepham-4-carboxylate-1-oxide, 2,2,2-trichloroethyl 7-cyanoacetamido-3-exomethylenecepham-4-carboxylate-1-oxide, diphenylmethyl 7-phthalimido-3-exomethylenecepham-4-carboxylate-1-oxide, p-nitrobenzyl 7-(2-carboxy-2-phenylacetamido)-3-exomethylenecephem-4-carboxylate-1-oxide.

According to the method of this invention, a 3-exomethylenecepham ester sulfoxide is reacted in an inert aprotic solvent at a temperature between about −90° and 20° C. with at least two molar equivalents of ozone and the intermediate oxidation products formed are decomposed either thermally or with a mild reducing agent, to provide a 3-hydroxy-3-cephem ester sulfoxide.

Solvents which can be employed in the present process are those solvents which themselves are inert to oxidation by ozone under the conditions employed for the ozonolysis of the 3-exomethylene group of the starting sulfoxide ester. Suitable solvents in the present process include the halogenated hydrocarbon solvents such as methylene chloride, ethylene dichloride, 1,1,2-trichloroethane, the nitriles for example acetonitrile, propionitrile, and butyronitrile, and esters such as methyl acetate or ethyl acetate. Mixtures of such solvents can also be used as well as aqueous solvents for example aqueous acetone.

In carrying out the process of this invention, it is preferred to use a protic co-solvent which serves as a proton source preventing the formation of cyclic peroxides. Suitable co-solvents which serve as proton sources include the alcohols such as methanol, ethanol, isopropanol, the carboxylic acids such as formic acid, acetic acid, and the higher homologs thereof for example propionic acid. Preferred co-solvents are methanol and acetic acid.

The amount of co-solvent added is not critical and generally between about two and three moles of co-solvent per mole of ester sulfoxide is sufficient.

The preferred temperature range is between about −40° and 5° C. The low temperatures, for example −80° to −90° can be achieved by means of liquid gases for example liquid nitrogen while the intermediate temperatures can be achieved by employing cooling baths with various dry ice-solvent combinations or ice-solvent combinations.

The concentration of the 3-exomethylenecepham ester sulfoxide in the solvent is not critical, however, concentrations of between about 2 and 20 percent appear to afford the best results.

In carrying out the ozonolysis at least about 2 moles of ozone per mole of 3-exomethylenecepham ester sulfoxide are used. Amounts of ozone in excess of 2 moles per mole of sulfoxide ester can be used without any untoward effect upon the yield of product. The ozone is generated in a standard ozone generator, such as one of those commercially available, which produce ozone by the action of an electric discharge on air or oxygen as it flows through the generator. The stream of ozone containing air or oxygen can be passed directly into the reaction vessel.

In general, the ozone stream is allowed to pass through the reaction mixture for a period of time sufficient to allow at least two equivalents of ozone to pass. Somewhat in excess of two equivalents is generally employed to ensure complete reaction. The reaction can be followed by removing aliquots from the reaction vessel from time to time and assaying the aliquot for the presence of starting material by chromatography. Thin layer chromatography is a convenient and quick way for determining the presence of starting material. Pilot runs also can be employed to determine the length of time of gas passage through reaction mixtures containing given amounts of starting material for common settings of the ozone generator. Alternatively, the amount of ozone generated in the air or oxygen stream can be predetermined for given voltage and flow settings on the ozonizer.

As previously mentioned, the intermediate oxidation products formed in situ during the ozonolysis, can be decomposed either thermally or by treating the reaction mixture with a mild reducing agent. When the ozonolysis of the 3-exomethylenecepham ester sulfoxide is carried out at temperatures much below 0°, for example at about −30° C., the reaction mixture can be warmed to between about 0° to about 45° C. to effect the decomposition. Alternatively, the ozonide can be thermally decomposed more rapidly by adding a higher boiling solvent to the reaction mixture and then evaporating the solvent from the reaction mixture with heat.

The intermediate oxidation products also can be decomposed by adding to the reaction mixture a mild reducing agent and preferably one which will not interfere with the isolation of the product. Suitable reducing agents include for example dimethyl sulfide, sulfur dioxide, sodium bisulfite and trimethyl phosphite. Dimethyl sulfide and sulfur dioxide are preferred reducing agents. In general, somewhat in excess of one mole of the reducing agent per mole of the starting material is used in the decomposition. The reducing agent is generally added at the temperature at which the ozonolysis has been carried out.

The intermediate oxidation products formed in situ are of unknown structure, however, it appear likely that one of the intermediates is the ozonide formed at the 3-exo double bond. Other oxidation products such as hydroperoxides are also possible.

The process of this invention provides high yields of the 3-hydroxy-3-cephem ester sulfoxides which are commonly on the order of between about 80 and 95 percent of the theoretical yield. The 3-hydroxy-3-cephem ester sulfoxides are generally obtained in such yields in a high state of purity directly from the reaction mixtures obtained via this process. The purity of the products is such that further purification prior to conversion to the 3-halo or 3-methoxy-3-cephem antibiotics is unnecessary.

The 3-hydroxy-3-cephem ester sulfoxides obtained by the process of this invention are highly stable compounds and accordingly are more useful as intermediates than the less stable 3-hydroxy-3-cephem esters obtained in the known process.

In a preferred embodiment of the process of this invention, p-nitrobenzyl 7-phenoxyacetamido-3-exomethylenecepham-4-carboxylate-1-oxide is dissolved in acetonitrile containing about 2.5 percent (v:v) of acetic acid and the solution is cooled to about −15° C. Ozone is passed through the reaction mixture until all starting material has reacted. Dimethyl sulfide is added to the reaction mixture which is then allowed to stir for 30 minutes at the reaction temperature of −15° C. The product, p-nitrobenzyl 7-phenoxyacetamido-3-hydroxy-3-cephem-4-carboxylate-1-oxide which forms as a precipitate is filtered. The filtered product is washed with cold solvent and vacuum dried.

In a further preferred embodiment of the present process, diphenylmethyl 7-phenylacetamido-3-exomethylenecepham-4-carboxylate-1-oxide is dissolved in methylene chloride containing about 0.5 percent (v:v) of methanol. The solution is cooled to −30° C. and ozone is bubbled through the cold solution until the starting materials has been oxidized. While maintaining the temperature at −30° C., sulfur dioxide is passed through the reaction mixture. The reaction mixture is then allowed to stir for about 30 minutes in the cold and the product is filtered and dried.

Among the starting materials which can be employed in the process of this invention, especially preferred are the esters of 7-phenoxyacetamido-3-exomethylenecepham-4-carboxylic acid-1-oxide and 7-phenylacetamido-3-exomethylenecepham-4-carboxylic acid-1-oxide. Preferred esters of these acids are p-nitrobenzyl, benzyl, 4-methoxybenzyl, 3,5-dimethoxybenzyl, diphenylmethyl (benzhydryl), and 2,2,2-trichloroethyl. An especially preferred ester group is the p-nitrobenzyl ester group. This ester group is preferred because it enhances the crystallinity and insolubility of the 3-hydroxy-3-cephem sulfoxides and thus aids in the isolation of the product.

The starting materials employed in the process of this invention are readily available materials prepared by known methods. For example, a 7-acylamido-3-exomethylenecepham-4-carboxylic acid or an ester thereof can be reacted with a peracid, for example m-chloroperbenzoic acid, perbenzoic acid, peracetic acid, to form the corresponding sulfoxide. The 3-exo double bond of the starting material is inert under the conditions of sulfoxide formation with such reagents and, consequently, the sulfoxide is prepared by the selective oxidation of the sulfide. Alternatively and preferably the sulfoxide ester starting materials can be obtained by the process described by S. Kukolja in co-pending application Ser. No. 536,280 filed Dec. 24, 1974 now abandoned. According to the described method, a 6-acylamidopenicillanic acid ester sulfoxide is reacted with an excess of N-chlorosuccinimide in a dry, inert organic solvent, such as 1,1,2-trichloroethane or toluene, at a temperature between about 70° and 100° C. to provide an azetidinone sulfinyl chloride. The azetidinone sulfinyl chloride is formally named 3-methyl-2-(2-chlorosulfinyl-4-oxo-3-acylamido-1-azetidinyl)-3-butenoic acid ester.

The azetidinone sulfinyl chloride is then reacted with a Lewis acid Friedel-Crafts type catalyst in a dry, inert organic solvent to effect cyclization and provide the 3-exomethylenecepham sulfoxide ester.

The foregoing reaction sequence is illustrated by the following reaction scheme.

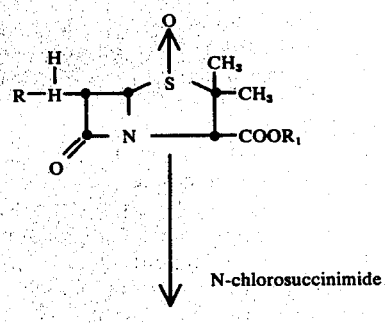

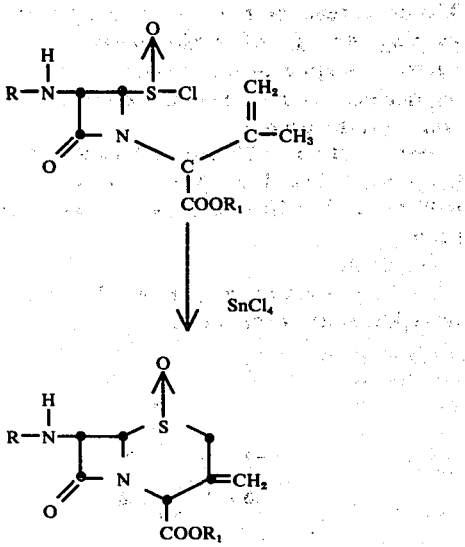

Lewis acid-Friedel Crafts catalysts which are useful in the cyclization of the azetidinone sulfinyl chloride include for example stannic chloride, zinc chloride, zinc bromide, titanium tetrachloride, and zirconium tetrachloride. Stannic chloride is a preferred catalyst in the cyclization. The cyclization is carried out in an inert solvent preferably an aprotic organic solvent for example aromatic hydrocarbons such as benzene, toluene, xylene, nitrobenzene, and the like; and halogenated aliphatic hydrocarbons such as methylene chloride, 1,2-dichlorethane and 1,1,2-trichloroethane.

The cyclization can be carried out at a temperature between about 20° and about 85° C.

In an example of the foregoing preparation of the starting materials useful in this process, a solution of p-nitrobenzyl 6-phenoxyacetamidopenicillanate sulfoxide in dry toluene is treated with 1.1 molar equivalents of N-chlorosuccinimide and the reaction mixture is refluxed for about 90 minutes. The reaction mixture containing p-nitrobenzyl 3-methyl-2-(2-chlorosulfinyl-4-oxo-3-phenoxyacetamido-1-azetidinyl)-3-butenoate, is cooled to a temperature of about 50° C. and 1.1 molar equivalents of anhydrous stannic chloride are added. The mixture thus obtained is stirred at room temperature for about 90 minutes. Water and ethyl acetate are added to the reaction mixture and the organic layer is separated. The organic layer containing the product is washed with dilute acid, dilute sodium bicarbonate, solution, and finally with brine. The washed organic layer is then dried and evaporated to yield p-nitrobenzyl 7-phenoxyacetamido-3-exomethylenecepham-4-carboxylate-1-oxide.

The products obtained by the process of this invention are useful intermediates for the preparation of 3-methoxy and 3-halo substituted cephalosporin antibiotic compounds. For example, p-nitrobenzyl 7-phenoxyacetamido-3-hydroxy-3-cephem-4-carboxylate-1-oxide is reacted with diazomethane to provide the 3-methoxy ester sulfoxide. The 3-methoxy ester sulfoxide is then reduced to the sulfide according to the reduction procedure disclosed in U.S. Pat. No. 3,641,041 issued Feb. 8, 1972. The sulfoxide reduction product, p-nitrobenzyl 7-phenoxyacetamido-3-methoxy-3-cephem-4-carboxylate, can be deesterified by reacting the ester with zinc and acid to effect the cleavage of the p-nitrobenzyl ester group and provide the antibiotic free acid compound. Alternatively, the sulfoxide reduction product can be reacted under the well known N-deacylation procedure employing $PCl_5$/methanol/water to obtain the 7-amino-3-cephem ester. The 7-amino ester can be acylated with the desired carboxylic acid by following conventional acylation procedures and the acylated nucleus can be deesterified to provide the desired N-acyl antibiotic compound.

The following examples are provided to further exemplify the process of this invention.

EXAMPLE 1 p-Nitrobenzyl 7-phenoxyacetamido-3-hydroxy-3-cephem-4-carboxylate-1-oxide

A solution of 1.25 g. of p-nitrobenzyl 7-phenoxyacetamido-3-exomethylenecepham-4-carboxylate-1-oxide in 150 ml. of methylene chloride containing about 0.31 ml. of methanol was degassed and cooled to −30° C. under nitrogen. Ozone was bubbled into the cold solution for about 4 minutes at −30° C., the blue reaction mixture was warmed to 0° C., degassed under reduced pressure, and was diluted with about 80 ml. of toluene. The diluted mixture was evaporated to a small volume under reduced pressure in a water bath maintained at about 45° C. The product, p-nitrobenzyl 7-phenoxyacetamido-3-hydroxy-3-cephem-4-carboxylate-1-oxide, which had formed as a gel in the concentrate was filtered and dried under vacuum at 60° C. The yield of the product was 1.1 g. (88 percent) and melted at about 130°–140° C.

Elemental analysis for $C_{22}H_{19}N_3O_9S$: Theory: C, 52.69; H, 3.81; N, 8.38. Found: C, 52.92; H, 4.08; N, 8.32.

EXAMPLE 2

Twenty grams of p-nitrobenzyl 7-phenoxyacetamido-3-exomethylenecepham-4-carboxylate-1-oxide were dissolved in 400 ml. of acetonitrile containing 10 ml. of acetic acid and the solution was cooled to −15° C. A stream of air containing approximately 2 percent of ozone from the ozone generator was passed through the cold solution at a rate of about 400 ml. per minute for one hour and 45 minutes. A small aliquot of the cold reaction solution was chromatographed on silica gel thin layer plates using ethyl acetate:acetic acid (20:1, v/v) for development. The developed chromatogram showed only a trace of starting material.

Dimethyl sulfide (3.0 ml.) was added to the cold reaction solution which was then allowed to stir for 30 minutes at −15° C. The product, p-nitrobenzyl 7-phenoxyacetamido-3-hydroxy-3-cephem-4-carboxylate-1-oxide, which had precipitated was filtered and washed on the filter with 100 ml. of cold acetonitrile. The product was dried in vacuo yielding a dry weight of 17.85 g. (89.1 percent).

EXAMPLE 3

A solution of 10.0 g. of p-nitrobenzyl 7-phenoxyacetamido-3-exomethylenecepham-4-carboxylate-1-oxide in 200 ml. of acetonitrile containing 2.4 ml. of methanol was cooled to a temperature of about −15° C. Ozone (2 percent in air) was passed through the cold solution for 50 minutes at a rate of about 400 ml. per minute. Dimethyl sulfide (3.0 ml.) was added and the reaction mixture was allowed to stir for 30 minutes while warming to a temperature of about 0° C. The precipitated product was filtered and washed on the filter with 100 ml. of cold acetonitrile. The washed precipitate was vacuum dried to yield 7.98 g of p-nitrobenzyl 7-phenoxyacetamido-3-hydroxy-3-cephem-4-carboxylate-1-oxide (79.5 percent yield).

EXAMPLE 4

Twenty grams of the starting material employed in the preceding examples were dissolved in 350 ml. of methylene chloride containing 35 ml. of acetic acid and the solution was cooled to a temperature between about −30° and −40° C. Ozone (approximately 2 percent concentration in air) was bubbled through the cold solution for 2.5 hours at a rate of approximately 400 ml. per minute. The chromatogram of an aliquot of the reaction mixture showed no starting material to be present. The reaction was allowed to stir for an additional 30 minutes while warming to about 0° C. The white flocculent product was filtered and washed on the filter with 150 ml. of methylene chloride. The washed product was dried in vacuo to yield 17.05 g. (85.1 percent yield) of the 3-hydroxy ester sulfoxide.

EXAMPLE 5

Twenty grams of the starting material employed in the preceding examples were dissolved in 350 ml. of methylene chloride containing 35 ml. of acetic acid and the solution was cooled to 0° C. Ozone (approximately 2 percent concentration in air) was bubbled through the cold reaction mixture for 2.5 hours at a rate of approximately 400 ml. per minute. During the passage of the ozone stream, the temperature was maintained at about 0° to 5° C. The reaction mixture was then allowed to stir for additional 45 minutes at about 0° to 5° C. and the product was filtered and washed with methylene chloride. The washed product was dried in vacuo to yield 16.39 g. (81.8 percent yield) of p-nitrobenzyl 7-phenoxyacetamido-3-hydroxy-3-cephem-4-carbozylate-1-oxide.

EXAMPLE 6

Diphenylmethyl 7-acetamido-3-exomethylenecepham-4-carboxylate-1-oxide is reacted with ozone by employing the temperature, solvent, and co-solvent employed in the reaction described by Example 1 to provide diphenylmethyl 7-acetamido-3-hydroxy-3-cephem-4-carboxylate-1-oxide.

EXAMPLE 7 p-Nitrobenzyl 7-phenylacetamido-3-exomethylenecepham-4-carboxylate-1-oxide is reacted with ozone by employing the reaction temperature, solvents and work-up procedures employed in the reaction described by Example 1 to provide p-nitrobenzyl 7-phenylacetamido-3-hydroxy-3-cephem-4-carboxylate-1-oxide.

EXAMPLE 8

A solution of p-nitrobenzyl 7-phthalimido-3-exomethylenecepham-4-carboxylate-1-oxide in 100 ml. of methylene chloride was cooled to a temperature of about −70° C. by means of a dry ice-acetone bath and a stream of ozone was bubbled into the cold solution until the reaction mixture became blue. Next, sulfur dioxide was passed through the cold reaction mixture for about two minutes. The reaction mixture was washed with a solution of sodium bisulfite, water and brine and was dried over anhydrous magnesium sulfate. The dried reaction mixture was evaporated to dryness yielding 4.0 g. of p-nitrobenzyl 7-phthalimido-3-hydroxy-3-cephem-4-carboxylate-1-oxide. The following nuclear magnetic resonance spectral data was obtained on the product.

nmr (CDCl$_3$): 3.75 and 4.4 (ABq, 2, J = 15 Hz CH$_2$—S), 418 (d, 1, J = 5 Hz), 5.4 (s, 2, CH$_2$ of ester), 6.08 (d, 1, J = Hz), and 7.4–8.3 (m, 8 aromatic H) delta.

We claim:
1. The process for preparing a 3-hydroxy-3-cephem sulfoxide ester of the formula

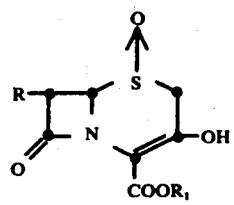

wherein R is H$_3$N$^+$—, phthalimido, succinimido, an acylamido group of the formula

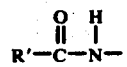

where R' is hydrogen, C$_1$ – C$_6$ alkyl, cyanomethyl, halomethyl; or an acylamino group of the formula

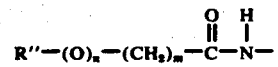

wherein R'' is phenyl or phenyl substituted by halogen, C$_1$–C$_4$ lower alkyl, C$_1$–C$_4$ lower alkoxy, nitro or carboxy, and m and n are independently 0 or 1; or R is substituted arylacylamido group of the formula

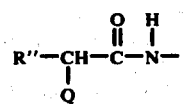

wherein R'' has the same meanings as defined above and Q is protected hydroxy, protected amino, carboxy, —SO$_2$NH$_2$ or the group —SO$_3$H; and R$_1$ is a carboxylic acid protecting group; which comprises (a) reacting in an inert solvent a 3-exomethylenecepham sulfoxide ester of the formula

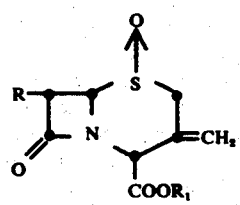

wherein R and R$_1$ have the same meanings as defined above, with at least two moles of ozone per mole of said 3-exomethylenecepham sulfoxide ester at a temperature between −90° and 20° C., and (b) decomposing the intermediate oxidation products.

2. The process of claim 1 wherein the intermediate oxidation products are decomposed with a reducing agent.

3. The process of claim 2 wherein the reducing agent is dimethyl sulfide.

4. The process of claim 2 wherein the reducing agent is sulfur dioxide.

5. The process of claim 1 wherein the intermediate oxidation products are decomposed thermally.

6. The process of claim 1 wherein the reaction of the 3-exomethylenecepham sulfoxide ester with ozone is carried out in the presence of a protic solvent.

7. The process of claim 1 wherein R is phenoxyacetamido, phenylacetamido or phthalimido.

8. The process of claim 7 wherein the 3-exomethylenecepham sulfoxide ester is p-nitrobenzyl 7-phenoxyacetamido-3-exomethylenecepham-4-carboxylate-1-oxide.

9. The process of claim 7 wherein the 3-exomethylenecepham sulfoxide ester is diphenylmethyl 7-phenylacetamido-3-exomethylenecepham-4-carboxylate-1-oxide.

10. The process of claim 7 wherein the 3-exomethylenecepham sulfoxide ester is p-nitrobenzyl 7-phthalimido-3-exomethylenecepham-4-carboxylate-1-oxide.

* * * * *

Notice of Adverse Decision in Interference

In Interference No. 100,022, involving Patent No. 4,031,084, S. Kukolja and D. O. Spry, PROCESS FOR CEPHALOSPORIN ANTIBIOTIC INTERMEDIATES, final judgment adverse to the patentees was rendered May 7, 1979, as to claims 1 through 10.

[*Official Gazette September 4, 1979.*]